(12) United States Patent
McKeon et al.

(10) Patent No.: US 7,195,901 B1
(45) Date of Patent: Mar. 27, 2007

(54) DIACYLGLYCEROL ACYLTRANSFERASE AND ITS USE TO PREFERENTIALLY INCORPORATE FATTY ACIDS INTO DIACYLGLYCEROL

(75) Inventors: Thomas A. McKeon, Richmond, CA (US); Xiaohua He, Albany, CA (US); Jiann-Tsyh Lin, Danville, CA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 145 days.

(21) Appl. No.: 10/861,616

(22) Filed: Jun. 3, 2004

(51) Int. Cl.
*C12N 9/10* (2006.01)
*C12N 1/19* (2006.01)
*C12N 1/21* (2006.01)
*C12Q 1/68* (2006.01)
*C12P 21/06* (2006.01)
*C07H 21/04* (2006.01)

(52) U.S. Cl. ............... 435/193; 435/254.11; 435/255.1; 435/252.3; 435/254.2; 435/6; 435/254.8; 435/69.1; 435/320.1; 536/23.2

(58) Field of Classification Search ................ 435/193, 435/23.2, 252.3; 536/23.2
See application file for complete search history.

(56) References Cited

U.S. PATENT DOCUMENTS

| 6,552,250 B1 | 4/2003 | Nykiforuk et al. |
| 6,559,359 B1 | 5/2003 | Laten |
| 6,583,302 B1 | 6/2003 | Erhan et al. |
| 6,620,986 B1 | 9/2003 | McKeon et al. |
| 2003/0074695 A1 | 4/2003 | Farese, Jr. et al. |

OTHER PUBLICATIONS

He, X. et al., "Cloning and Characterization of a cDNA Encoding Diacylglycerol Acyltransferase from Castor Bean," Lipids (2004) 39(2):1-8.

*Primary Examiner*—Rebecca E. Prouty
*Assistant Examiner*—Iqbal Chowdhury
(74) *Attorney, Agent, or Firm*—Elizabeth R. Sampson; David R. Nicholson; John D. Fado

(57) ABSTRACT

The gene for the diacylglycerol acyltransferase (DGAT) from *Ricinus communis* L., the castor plant, has been isolated, cloned, and used to transform other plants and microorganisms. When the gene is expressed in a heterologous system, the corresponding DGAT protein is active and shows unusual and selective action for hydroxylated fatty acyl glycerides. DGAT carries out the final step in castor oil biosynthesis, and is believed to be largely responsible for many of the attributes of castor oil, making it an excellent candidate for industrial uses. This invention makes it possible to enhance the oil-producing capacity of other plants and micro-organisms.

8 Claims, 8 Drawing Sheets

```
BnDGAT    ...MAILDSG GVAVPPTENG ...V.ADLDR LHRRKSSS.. ..DSSNGLLS  39
AtDGAT    ...MAILDSA GVTT.VTENG GGEF.VDLDR LRRRKSRS.. ..DSSNGLLL  41
TmDGAT    ...MA■■■ Q    MSGHG D....SDLNN FRRRKPSSSV IEPSSSGFTS   43
RcDGAT    ...MTILETP ETLGVISSSA T■■■DL     RRRR■■  ..    GALA    39
NtDGAT    MVIMELPESV EMTTTTTTSG I■■■DL     RRRRGSNG  .■■ASAI     49

BnDGAT    .......DTS PSDDVGAAAA ERDRVDSAAE EEAQGTAN.. ..LAGGDAET  78
AtDGAT    SGS...DNNS PSDDVGAPAD VRDRIDSVVN DDAQGTAN.. ..LAGDNNGG  84
TmDGAT    ........TN GVPATGHVAE NRDQD■■■■ E   SVN.. ..LIGNGGGV   81
RcDGAT    DLASKFDDDD DVRSEDSAEN IIEDPVAAVT ELATAKSNGK DCVANSNKDK  89
Nt■■■■ A      DRR DVCGSGAGLE TVNERSKSVG ESSDVIRK.. ..EDDRNDNV   95

BnDGAT    RESAGG.... .......DVR FTYRPSVPAH RRTRESPLSS DAIFKQSHAG  117
AtDGAT    GDNNGGGRGG GEGRGNADAT FTYRPSVPAH RRARESPLSS DAIFKQSHAG  134
TmDGAT    VIGNEEKQVG .....ETDIR FTYRPSFPAH RRVRESPLSS DAIFKQSHAG  126
RcDGAT    IDSHGG.... ......SSDFK LAYRPSVPAH RSLKESPLSS DLIFKQSHAG  130
NtDGAT    ANGEESKSTE TT...TTPFK FAYRASAPAH RRIKESPLSS DAIFKQSHAG  142

BnDGAT    LFNLCVVVLV AVNSRLIIEN LMKYGWLIRT DFWFSSTSLR DWPLFMCCLS  167
AtDGAT    LFNLCVVVLI AVNSRLIIEN LMKYGWLIRT DFWFSSRSLR DWPLFMCCIS  184
TmDGAT    LFNLCIVVLI AVNSRLIIEN LMKYGWLIDT GFWFNSRSLG DWSIFMCCLT  176
RcDGAT    LFNLCIVVLV AVNSRLIIEN LMKYGWLIKT GFWFSSRSLR DWPLFMCCLS  180
NtDGAT    LFNLCVVVLI AVNSRLIIEN LMKYGLLIRA GFWFSSKSLR DWPLLMCCLS  192

BnDGAT    LSVFPLAAFT VEKMVLQKFI SEPVAIILHV IITMTEVLYP VYVTLRCDSA  217
AtDGAT    LSIFPLAAFT VEKLVLQKYI SEPVVIFLHI IITMTEVLYP VYVTLRCDSA  234
TmDGAT    LPIFPLAAFI VEKLVQRNHI SELVAVLLHV IVSTAAVLYP VIVILTCDSV  226
RcDGAT    LPVFPLAAYL VEKAAYRKYI SPPIVIFLHV IITSAAVLYP ASVILSCESA  230
NtDGAT    LQILPLAAFL VEKLAQQRHL TERAVVTLHI TITTAAILYP VLVILGCDSA  242

BnDGAT    FLSGVTLMLL TCIVWLKLVS YAHTSYDIRT LANSADK..V DP.....EIS  260
AtDGAT    FLSGVTLMLL TCIVWLKLVS YAHTSYDIRS LANAADK..A NP.....EVS  277
TmDGAT    YMSGVVLMLF GCIMWLKLVS YAHTSSDIRT LAKSGY■■■   HP    VSCS  276
RcDGAT    FLSGVTLMEL ACMVWLKLVS YAHTNYDMRA IADTI■■■A S  .TEYC    279
NtDGAT    FLFGVILMLV ACIVWMKLVS YAHTNHDMRQ LAKSTDKDET SDG....DFS  288

BnDGAT    YYVSLKSLAY FMVAPTLCYQ PSYPRSPCIR KGWVARQLAK LVIFTGLMGF  310
AtDGAT    YYVSLKSLAY FMVAPTLCYQ PSYPRSACIR KGWVARQFAK LVIFTGLMGF  327
TmDGAT    YDVSLKSLAY FMVAPTLCYQ PSYPRSSCIR KGWVVRQFVK LIVFIGLMGF  326
RcDGAT    HDVSFKTLAY FMVAPTLCYQ PSYPRTAFIR KGWVFRQFVK LIIFTGFMGF  329
NtDGAT    YDVSFKSLAY FMVAPTLCYQ LSYPHTPCIR KGWVARQFIK LVIFTGLMGF  338

BnDGAT    IIEQYINPIV RNSKHPLKGD LLYAIERVLK LSVPNLYVWL CMFYCFFHLW  360
AtDGAT    IIEQYINPIV RNSKHPLKGD LLYAIERVLK LSVPNLYVWL CMFYCFFHLW  377
TmDGAT    IIEQYINPIV RNSKHPLKGD FLYAIERVLK LSVPNLYVWL CMFYSFFHLW  376
RcDGAT    IIEQYINPIV QNSQHPLKGD LLYAIERVLK LSVPNLYVWL CLFYCFFHLW  379
NtDGAT    IIEQYINPIV QNSQHPLKGN LLYAIERVLK LSVPNLYVWL CMFYCFFHLW  388

BnDGAT    LNILAELLCF GDREFYKDWW NAKSVGDYWR MWNMPVHKWM VRHVYFPCLR  410
AtDGAT    LNILAELLCF GDREFYKDWW NAKSVGDYWR MWNMPVHKWM VRHIYFPCLR  427
TmDGAT    LNILAELLRF GDREFYKDWW NAKTVAEYWK MWNMPVHRWM VRHLYFPCLR  426
RcDGAT    LNIVAELLRF GDREFYKDWW NAKTVEEYWR MWNMPVHKWM VRHIYFPCLR  429
NtDGAT    LNILAELLCF GDREFYKDWW NAKTIDEYWR MWNMPVHKWM VRHIYFPCLR  438

BnDGAT    IKIPKVPAII IAFLVSAVFH ELCIAVPCRL FNLWAFMGIM FQVPLVFITN  460
AtDGAT    SKIPKTLAII IAFLVSAVFH ELCIAVPCRL FKLWAFLGIM FQVPLVFITN  477
TmDGAT    NGIPKEGAII IAFLVSGAFH ELCIAVPCHV FKLWAFIGIM FQVPLVLITN  476
RcDGAT    RKIPRGVAIV IAFFVSAVFH ELCIAVPCHM FKLWAFFGIM FQIPLVVITN  479
NtDGAT    NGIPKGVAIL IAFLVSAVFH ELCIAVPCRL FKWWAFMGIM FQVPLVILTN  488

BnDGAT    FLQERFG.SM VGNMIFGSAS CIFQQPMCGL LYYHDLMNRK GSMS       503
AtDGAT    YLQERFG.ST VGNMIFWFIF CIFQQPMCVL LYYHDLMNRK GSMS       520
TmDGAT    YLQEKFSNSM VGNMIFWFIF CILQQPMCVL LYYHDLINLK EK..       518
RcDGAT    YFQRKFRSSM VGNMIFWFFF CILQQPMCVL LYYHDLMNRD GN..       521
NtDGAT    FLQNKFQSSM VGNMMFWCFF CILQQPMCVL LYYHDVMNRK SSAR       532
```

FIG. 1

SEQUENCE LISTING

<160> NUMBER OF SEQ ID NOS: 11

<210> SEQ ID NO 1
<211> LENGTH: 2067
<212> TYPE: DNA
<213> ORGANISM: Ricinus Communis
<220> FEATURE:
<221> NAME/KEY: CDS
<222> LOCATION: (267)..(1829)

<400> SEQUENCE: 1

```
ggacactgac atggactgaa ggagtagaaa cttcttcttc tgctgctgtt cctctctcct      60
ccaccgccac gctcacctct ctttgcatga cataatacta ttgttcttat tatcattttc     120
actctttaaa tacaaacatc aattattcct tttctatcaa acacatgtat tctattctct     180
cgtcgtctag attctcatct tcattgaatc ctccttctta gcgtgtcttt gtccacttct     240
tttgggcacc gacgttttta atctcc atg acg att ctc gaa acg cca gaa act      293
                              Met Thr Ile Leu Glu Thr Pro Glu Thr
                                1               5 ctt ggc gtc atc tcc tcc tcc gcc act tcc gat ctc aac ctc tct ctc       341
Leu Gly Val Ile Ser Ser Ser Ala Thr Ser Asp Leu Asn Leu Ser Leu
 10              15                  20                  25 cga cgt aga cgg acc tca aat gac tcc gat ggt gca ctt gct gat ttg       389
Arg Arg Arg Arg Thr Ser Asn Asp Ser Asp Gly Ala Leu Ala Asp Leu
                 30                  35                  40 gct tcg aag ttt gat gat gat gac gac gta aga tcg gaa gat tct gct       437
Ala Ser Lys Phe Asp Asp Asp Asp Asp Val Arg Ser Glu Asp Ser Ala
             45                  50                  55 gaa aat att atc gaa gat cct gta gca gcg gtt act gaa ttg gcg aca       485
Glu Asn Ile Ile Glu Asp Pro Val Ala Ala Val Thr Glu Leu Ala Thr
         60                  65                  70 gca aag agt aac gga aaa gac tgt gtt gcc aat agt aat aag gat aaa       533
Ala Lys Ser Asn Gly Lys Asp Cys Val Ala Asn Ser Asn Lys Asp Lys
 75              80                  85 att gat agc cat gga gga tca tcg gat ttt aaa ctt gca tat agg cct       581
Ile Asp Ser His Gly Gly Ser Ser Asp Phe Lys Leu Ala Tyr Arg Pro
 90              95                  100                 105 tcg gtt cca gct cac cgg tca ctt aag gag agt ccg ctt agc tct gat       629
Ser Val Pro Ala His Arg Ser Leu Lys Glu Ser Pro Leu Ser Ser Asp
                 110                 115                 120 tta ata ttt aaa caa agt cat gca ggt ctg ttt aac ctt tgt ata gta       677
Leu Ile Phe Lys Gln Ser His Ala Gly Leu Phe Asn Leu Cys Ile Val
             125                 130                 135 gtg ctc gta gct gtt aac agc agg ctc atc att gag aat tta atg aag       725
Val Leu Val Ala Val Asn Ser Arg Leu Ile Ile Glu Asn Leu Met Lys
         140                 145                 150 tat ggc tgg tta att aag acg ggc ttt tgg ttt agt tca aga tca ttg       773
Tyr Gly Trp Leu Ile Lys Thr Gly Phe Trp Phe Ser Ser Arg Ser Leu
 155             160                 165 aga gat tgg ccg ctt ttt atg tgc tgt ctt tct ctc cca gta ttc ccc       821
Arg Asp Trp Pro Leu Phe Met Cys Cys Leu Ser Leu Pro Val Phe Pro
170              175                 180                 185 ctt gct gcc tat cta gtt gag aag gcc gca tat cga aaa tat ata tct       869
Leu Ala Ala Tyr Leu Val Glu Lys Ala Ala Tyr Arg Lys Tyr Ile Ser
                 190                 195                 200 ccg cct att gtt att ttc ctt cat gtg atc atc acc tca gca gct gtt       917
Pro Pro Ile Val Ile Phe Leu His Val Ile Ile Thr Ser Ala Ala Val
             205                 210                 215 ttg tac cca gct tct gta att ctc agt tgt gaa tct gct ttt tta tct       965
Leu Tyr Pro Ala Ser Val Ile Leu Ser Cys Glu Ser Ala Phe Leu Ser
         220                 225                 230 ggt gtc aca ttg atg gaa ctt gct tgt atg gta tgg ttg aaa ttg gta      1013
Gly Val Thr Leu Met Glu Leu Ala Cys Met Val Trp Leu Lys Leu Val
 235             240                 245 tcc tat gca cat aca aac tat gat atg aga gcg atc gct gac acc att      1061
Ser Tyr Ala His Thr Asn Tyr Asp Met Arg Ala Ile Ala Asp Thr Ile
250              255                 260                 265
```

```
cat aag gaa gat gca tcc aat tct tct agt aca gag tat tgt cat gat    1109
His Lys Glu Asp Ala Ser Asn Ser Ser Ser Thr Glu Tyr Cys His Asp
            270                 275                 280 gtg agc ttt aag act ttg gcg tac ttc atg gtc gca ccc aca tta tgt    1157
Val Ser Phe Lys Thr Leu Ala Tyr Phe Met Val Ala Pro Thr Leu Cys
        285                 290                 295 tac cag cca agt tat cct cgc aca gca ttt att aga aag ggc tgg gtg    1205
Tyr Gln Pro Ser Tyr Pro Arg Thr Ala Phe Ile Arg Lys Gly Trp Val
    300                 305                 310 ttc cgt caa ttt gtc aaa cta ata att ttt aca gga ttc atg gga ttt    1253
Phe Arg Gln Phe Val Lys Leu Ile Ile Phe Thr Gly Phe Met Gly Phe
315                 320                 325 atc ata gaa caa tac atc aat cct atc gtc cag aat tct caa cac cct    1301
Ile Ile Glu Gln Tyr Ile Asn Pro Ile Val Gln Asn Ser Gln His Pro
330                 335                 340                 345 tta aaa ggg gat ctc tta tat gcc att gag agg gtt ctg aag ctc tca    1349
Leu Lys Gly Asp Leu Leu Tyr Ala Ile Glu Arg Val Leu Lys Leu Ser
            350                 355                 360 gtt ccg aat tta tat gtg tgg ctc tgc ttg ttc tac tgc ttt ttt cac    1397
Val Pro Asn Leu Tyr Val Trp Leu Cys Leu Phe Tyr Cys Phe Phe His
        365                 370                 375 ctg tgg ttg aat ata gtt gct gag ctc ctt cgc ttc ggt gac cgg gag    1445
Leu Trp Leu Asn Ile Val Ala Glu Leu Leu Arg Phe Gly Asp Arg Glu
    380                 385                 390 ttc tac aaa gat tgg tgg aat gca aaa act gtt gag gag tac tgg agg    1493
Phe Tyr Lys Asp Trp Trp Asn Ala Lys Thr Val Glu Glu Tyr Trp Arg
395                 400                 405 atg tgg aat atg cct gtt cac aag tgg atg gtt cgc cat atc tac ttc    1541
Met Trp Asn Met Pro Val His Lys Trp Met Val Arg His Ile Tyr Phe
410                 415                 420                 425 cca tgc cta cgt cgt aaa ata cca agg ggg gta gca ata gtt att gct    1589
Pro Cys Leu Arg Arg Lys Ile Pro Arg Gly Val Ala Ile Val Ile Ala
            430                 435                 440 ttc ttc gtt tca gct gta ttt cat gag ttg tgc att gct gtt cct tgc    1637
Phe Phe Val Ser Ala Val Phe His Glu Leu Cys Ile Ala Val Pro Cys
        445                 450                 455 cac atg ttc aaa ctt tgg gct ttt ttt gga ata atg ttt cag att cct    1685
His Met Phe Lys Leu Trp Ala Phe Phe Gly Ile Met Phe Gln Ile Pro
    460                 465                 470 tta gtt gtg atc act aat tat ttt caa agg aag ttc aga agc tca atg    1733
Leu Val Val Ile Thr Asn Tyr Phe Gln Arg Lys Phe Arg Ser Ser Met
475                 480                 485 gtg gga aat atg atc ttc tgg ttc ttt ttc tgc att ctc ggc caa cct    1781
Val Gly Asn Met Ile Phe Trp Phe Phe Phe Cys Ile Leu Gly Gln Pro
490                 495                 500                 505 atg tgt gta ctg ttg tat tac cat gac cta atg aat cgc gat ggg aac    1829
Met Cys Val Leu Leu Tyr Tyr His Asp Leu Met Asn Arg Asp Gly Asn
            510                 515                 520 tgaaccatgg gctcagtcca gatatgggta caccttccaa gatgttattt tcgtgagtga    1889
agactgcacc acagtgttgt tcttgttaca caatccccat tgacagagta ggttaatcgt    1949
cagtttcagg agataagaca caattttgaa agtacagcag aggctgctat taatgtatca    2009
tgttgagttt ctgttatgtt atgttattct tttttaatct caaaaaaaaa aaaaaaaa      2067

<210> SEQ ID NO 2
<211> LENGTH: 521
<212> TYPE: PRT
<213> ORGANISM: Ricinus Communis
```

```
<400> SEQUENCE: 2

Met Thr Ile Leu Glu Thr Pro Glu Thr Leu Gly Val Ile Ser Ser Ser
 1               5                  10                  15

Ala Thr Ser Asp Leu Asn Leu Ser Leu Arg Arg Arg Arg Thr Ser Asn
                20                  25                  30

Asp Ser Asp Gly Ala Leu Ala Asp Leu Ala Ser Lys Phe Asp Asp Asp
                35                  40                  45

Asp Asp Val Arg Ser Glu Asp Ser Ala Glu Asn Ile Ile Glu Asp Pro
        50                  55                  60

Val Ala Ala Val Thr Glu Leu Ala Thr Ala Lys Ser Asn Gly Lys Asp
65                  70                  75                  80

Cys Val Ala Asn Ser Asn Lys Asp Lys Ile Asp Ser His Gly Gly Ser
                85                  90                  95

Ser Asp Phe Lys Leu Ala Tyr Arg Pro Ser Val Pro Ala His Arg Ser
                100                 105                 110

Leu Lys Glu Ser Pro Leu Ser Ser Asp Leu Ile Phe Lys Gln Ser His
                115                 120                 125

Ala Gly Leu Phe Asn Leu Cys Ile Val Val Leu Ala Val Asn Ser
                130                 135                 140

Arg Leu Ile Ile Glu Asn Leu Met Lys Tyr Gly Trp Leu Ile Lys Thr
145                 150                 155                 160

Gly Phe Trp Phe Ser Ser Arg Ser Leu Arg Asp Trp Pro Leu Phe Met
                165                 170                 175

Cys Cys Leu Ser Leu Pro Val Phe Pro Leu Ala Ala Tyr Leu Val Glu
                180                 185                 190

Lys Ala Ala Tyr Arg Lys Tyr Ile Ser Pro Pro Ile Val Ile Phe Leu
                195                 200                 205

His Val Ile Ile Thr Ser Ala Ala Val Leu Tyr Pro Ala Ser Val Ile
                210                 215                 220

Leu Ser Cys Glu Ser Ala Phe Leu Ser Gly Val Thr Leu Met Glu Leu
225                 230                 235                 240

Ala Cys Met Val Trp Leu Lys Leu Val Ser Tyr Ala His Thr Asn Tyr
                245                 250                 255

Asp Met Arg Ala Ile Ala Asp Thr Ile His Lys Glu Asp Ala Ser Asn
                260                 265                 270

Ser Ser Ser Thr Glu Tyr Cys His Asp Val Ser Phe Lys Thr Leu Ala
                275                 280                 285

Tyr Phe Met Val Ala Pro Thr Leu Cys Tyr Gln Pro Ser Tyr Pro Arg
                290                 295                 300

Thr Ala Phe Ile Arg Lys Gly Trp Val Phe Arg Gln Phe Val Lys Leu
305                 310                 315                 320

Ile Ile Phe Thr Gly Phe Met Gly Phe Ile Ile Glu Gln Tyr Ile Asn
                325                 330                 335

Pro Ile Val Gln Asn Ser Gln His Pro Leu Lys Gly Asp Leu Leu Tyr
                340                 345                 350

Ala Ile Glu Arg Val Leu Lys Leu Ser Val Pro Asn Leu Tyr Val Trp
                355                 360                 365

Leu Cys Leu Phe Tyr Cys Phe Phe His Leu Trp Leu Asn Ile Val Ala
                370                 375                 380

Glu Leu Leu Arg Phe Gly Asp Arg Glu Phe Tyr Lys Asp Trp Trp Asn
385                 390                 395                 400

Ala Lys Thr Val Glu Glu Tyr Trp Arg Met Trp Asn Met Pro Val His
                405                 410                 415
```

```
Lys Trp Met Val Arg His Ile Tyr Phe Pro Cys Leu Arg Arg Lys Ile
            420                 425                 430

Pro Arg Gly Val Ala Ile Val Ile Ala Phe Phe Val Ser Ala Val Phe
            435                 440                 445

His Glu Leu Cys Ile Ala Val Pro Cys His Met Phe Lys Leu Trp Ala
            450                 455                 460

Phe Phe Gly Ile Met Phe Gln Ile Pro Leu Val Val Ile Thr Asn Tyr
465                 470                 475                 480

Phe Gln Arg Lys Phe Arg Ser Ser Met Val Gly Asn Met Ile Phe Trp
                485                 490                 495

Phe Phe Phe Cys Ile Leu Gly Gln Pro Met Cys Val Leu Leu Tyr Tyr
            500                 505                 510

His Asp Leu Met Asn Arg Asp Gly Asn
            515                 520

<210> SEQ ID NO 3
<211> LENGTH: 20
<212> TYPE: DNA
<213> ORGANISM: Artificial
<220> FEATURE:
<223> OTHER INFORMATION: 5' end primer used to amplify the FAH gene

<400> SEQUENCE: 3
cgccgcacac gaagcctcct                                              20

<210> SEQ ID NO 4
<211> LENGTH: 34
<212> TYPE: DNA
<213> ORGANISM: Artificial
<220> FEATURE:
<223> OTHER INFORMATION: 3' end primer used to amplify the FAH gene

<400> SEQUENCE: 4
aggctacatg acactttttt aatacttgtt ccgg                              34

<210> SEQ ID NO 5
<211> LENGTH: 25
<212> TYPE: DNA
<213> ORGANISM: Artificial
<220> FEATURE:
<223> OTHER INFORMATION: 5' end primer used to amplify the actin gene

<400> SEQUENCE: 5 agggataac caccccatga atcca                                         25

<210> SEQ ID NO 6
<211> LENGTH: 25
<212> TYPE: DNA
<213> ORGANISM: Artificial
<220> FEATURE:
<223> OTHER INFORMATION: 3' end primer used to amplify the actin gene

<400> SEQUENCE: 6
tgcatggtct cctgatacgg ccaag                                        25

<210> SEQ ID NO 7
<211> LENGTH: 24
<212> TYPE: DNA
<213> ORGANISM: Artificial
<220> FEATURE:
<223> OTHER INFORMATION: 3' end primer used to amplify the full-length
      RcDAT cDNA
```

-continued

```
<400> SEQUENCE: 7
ctgagagctt cagaaccctc tcaa                                           24

<210> SEQ ID NO 8
<211> LENGTH: 18
<212> TYPE: DNA
<213> ORGANISM: Artificial
<220> FEATURE:
<223> OTHER INFORMATION: degenerate primer based on highly conserved
      amino sequence region, APTLCY of DGATs, and used to clone the
      RcDGAT gene.

<400> SEQUENCE: 8
gckccmacay trtgttat                                                  18

<210> SEQ ID NO 9
<211> LENGTH: 24
<212> TYPE: DNA
<213> ORGANISM: Artificial
<220> FEATURE:
<223> OTHER INFORMATION: degenerate primer based on the highly conserved
      amino sequence region, WNMPVHKW of DGATs, and used to clone the
      RcDGAT gene.

<400> SEQUENCE: 9
ccayttrtga acaggcatat tcca                                           24

<210> SEQ ID NO 10
<211> LENGTH: 30
<212> TYPE: DNA
<213> ORGANISM: Artificial
<220> FEATURE:
<223> OTHER INFORMATION: 5' end primer used to amplify the RcDGAT gene
      and clone this gene into the yeast vector pYES2.1/V5-His-TOPO for
      expression of RcGAT gene in yeast cells.

<400> SEQUENCE: 10
gaccatgggg attctcgaaa cgccagaaac                                     30

<210> SEQ ID NO 11
<211> LENGTH: 24
<212> TYPE: DNA
<213> ORGANISM: Artificial
<220> FEATURE:
<223> OTHER INFORMATION: 3' end primer used to amplify the RcDGAT gene
      and clone this gene into the yeast vector pYES2.1/V5-His-TOPO for
      expression of RcDGAT gene in yeast cells.

<400> SEQUENCE: 11
gttcccatcg cgattcatta ggtc                                           24
```

DIACYLGLYCEROL ACYLTRANSFERASE AND ITS USE TO PREFERENTIALLY INCORPORATE FATTY ACIDS INTO DIACYLGLYCEROL

BACKGROUND OF THE INVENTION

1. Field of the Invention

The present invention relates to biodegradable lubricants and greases.

2. Description of the Art

Biodegradable lubricants and greases are desirable because they provide an alternative to petroleum based lubricants which are toxic to the environment and which are increasingly difficult to dispose of safely and economically. Moreover, there has been an increasing demand for "green" lubricants in recent years due to increasingly strict government regulations controlling and restricting the use of traditional petroleum-based lubricants. Vegetable oils provide good alternatives because they are non-toxic, readily biodegradable, readily renewable, safe to handle, and environmentally friendly.

The triacylglycerol structure of vegetable oil, which is amphiphilic in character, accounts for its potential as an excellent candidate for use as a functional lubricant. Triacylglycerol molecules typically orient themselves with their polar ends making contact with any solid surface, becoming closely packed together and forming a surface film on the material being lubricated. In addition, the vegetable oil structure provides sites for various functional groups that permit the oils to be modified for improved technical properties such as thermo-oxidative and low temperature stability. These properties make vegetable oils very attractive for industrial applications that have potential for environmental contact through accidental leakage or through ordinary disposal.

The oil from castor seed (*Ricinus communis*) is particularly useful because it is extremely viscous and is therefore an excellent source for biodegradable lubricants and greases. Worldwide, the annual production of castor oil is about 460,000 tons (1.1 million tons of seeds) produced mainly in India, Brazil and China (http://www.hort.purdue.edu/newcrop/). The U.S. spends over $50 million annually to import castor for industrial applications including such diverse products as lubricants, greases, plasticizers, cosmetics, pharmaceuticals, paints, plastics, coatings, antifungal compounds, shampoo, and thermopolymers. Conventional domestic production of castor oil, however, is seriously hindered due to the presence of a toxic protein, ricin, as well as various allergenic albumins.

The usefulness and versatility of castor oil is due to the fact that approximately 90% of the fatty acid composition in castor oil is ricinoleic acid, an hydroxyl fatty acid, which is naturally present in few other plants and then only in small amounts.

Currently, one of the major issues in plant biotechnology is the elucidation of how plants assemble various compounds and specifically how to isolate and purify such compounds, particularly when they have useful industrial applications such as ricinoleate. In plant lipid metabolism, for example, it is possible to isolate various genes which can then be manipulated for the purpose of altering fatty acid composition. Manipulation of how these genes operate underlies future progress in developing crops containing high levels of hydroxylated fatty acids.

In fact, there have already been attempts to produce and extract ricinoleate from transgenic plants which do not produce the noxious components incident to castor oil production. These efforts have focused on plants such as tobacco and *Arabidopsis*, and have been mostly directed to the expression of a cDNA encoding fatty acyl hydroxylase (FAH), an enzyme catalyzing the hydroxylation of oleate to ricinoleate in castor. Only low levels of hydroxy fatty acids have been achieved using this approach, however, which suggests that the FAH gene itself is not sufficient to produce the high level of ricinoleate characteristic of castor.

A more productive approach, therefore, is necessary.

SUMMARY OF THE INVENTION

The invention described here is the identification, cloning, and expression of the gene sequence for diacylglycerol acyltransferase from *R. communis* (RcDGAT). This enzyme incorporates the third and final fatty acid into a diacylglycerol (DAG) resulting in a triacylglycerol. The unique feature of the RcDGAT gene product is its ability to preferentially incorporate ricinoleic acid and other hydroxy fatty acids into the diacylglycerol fraction.

RcDGAT is significant because it carries out the final step in castor oil biosynthesis. It preferentially synthesizes triacyglycerols containing hydroxyl fatty acids, and also operates as a rate-limiting factor for castor oil biosynthesis. This invention makes it possible to produce high-viscosity ricinoleate without noxious byproducts such as ricin and various harmful allergens that remain as residues after processing castor seed for castor oil. This invention paves the way for a safe and inexpensive source of castor oil in the U.S. and world markets.

A major advantage of this invention is that it can be used to create new and improved plants or micro-organisms that can produce ricinoleate without the concomitant contamination from ricin and other noxious allergens that are present in castor seed, thus reducing health risks to agricultural and industrial workers.

Another advantage is that this invention can be used to engineer temperate-climate oil seed crops to make new and improved castor oil substitutes.

Still another advantage is that this invention can be used to engineer new and improved lubricants for a wide range of industrial applications.

Another advantage is that the invention will permit the creation of various transgenic organisms incorporating the RcDGAT gene with the FAH gene, thus creating additional sources of TAG which contains high levels of ricinoleate without the possibility of ricin and allergen contamination.

Yet another advantage is that the invention will allow development of crops that can incorporate other polar fatty acids, such as epoxy fatty acids, expanding the types of fatty acids that can be produced in agricultural crops.

Other objects and advantages of the invention will become apparent in the disclosure which follows.

BRIEF DESCRIPTION OF THE DRAWINGS

FIG. 1 shows alignments of deduced amino acid sequences for various DGATs. Alignments were generated using Clustal W program in GCG output format (freely available at http://pbil.ibcp.fr/NPSA/npsa_prosite.html), and the GeneBank accession numbers for the listing DGATs are as follows: AtDGAT from *A. thaliana*, AF 051849; BnDGAT from *B. napus*, AF 164434; NtDGAT from *N. tobacum*, AF 129003, RcDGAT from *R. communis*, AY366496; TmDGAT from *T. majus*, AY 084052. The identical residues among the five proteins are in bold and the transmembrane segments are boxed. N-glycosylation sites are highlighted. The binding-protein-dependent transport systems inner membrane component signature is shaded in gray. The potential protein kinase phosphorylation sites are listed as below:

a) cAMP- and cGMP-dependent protein kinase phosphorylation site, amino acid residues

27–30; 28–31 b) Protein kinase C phosphorylation site, amino acid residues

24–26; 73–75; 85–87; 112–114; 165–167; 168–170; 283–285 c) Casein kinase II phosphorylation site, amino acid residues

2–5; 30–33; 43–46; 85–88; 112–115; 168–171; 236–239; 254–257; 274–277; 403–406 d) Tyrosine kinase phosphorylation site, amino acid residues

388–395

Figure 2A:
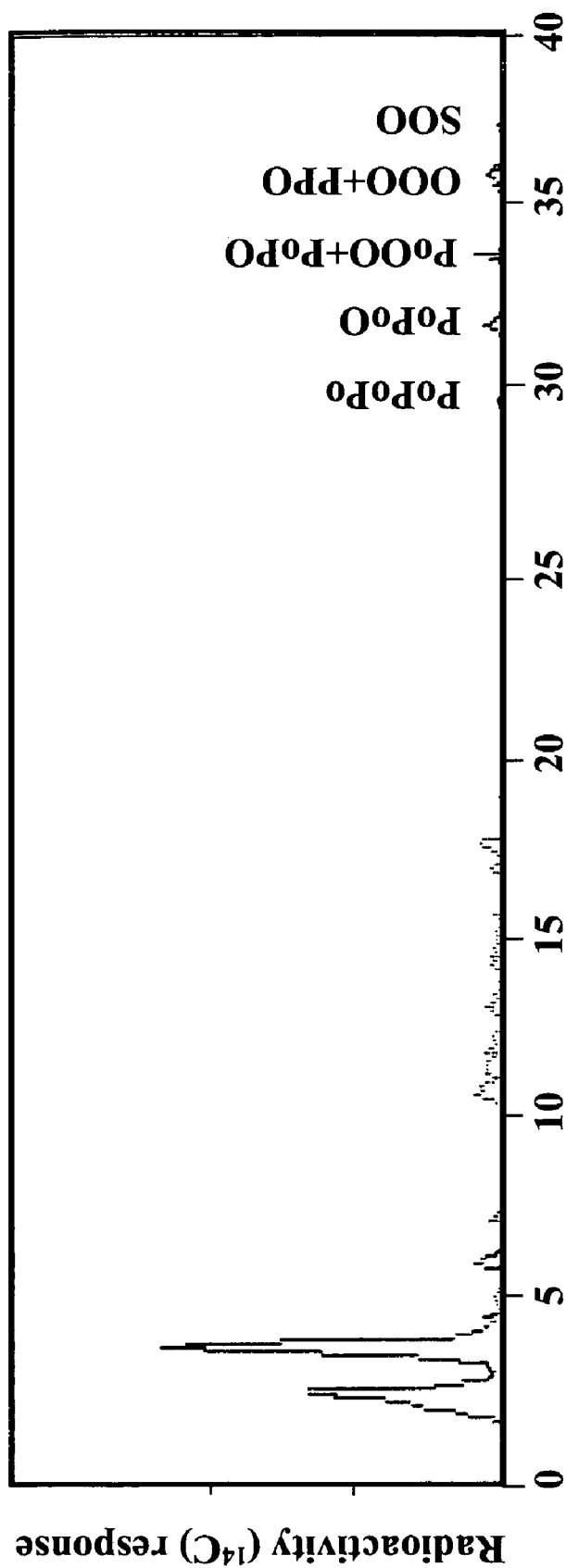

FIGS. 2A and B show triacylglycerols produced in yeast microsomes. Batches of microsomes (100 µg of total protein) extracted from yeast cells were incubated with $^{14}C$-oleoyl-CoA in 100 µl of 0.1 M Tris-HCl, pH7.0 containing 20% glycerol for 15 min at 30° C. Assays were terminated by addition of $CHCl_3/CH_3OH$ (1:2, v/v) and lipids were extracted. The C18 HPLC radiochromatograms show the separation of molecular species of TAG from incubations of yeast microsomes expressing α-galactosidase (A) and RcDGAT (B). The molecular species of TAG are given as the abbreviations of their fatty acid constituents: Po—palmitoleate; P—palmitate; O—Oleate; S—stearate.

Figure 3:
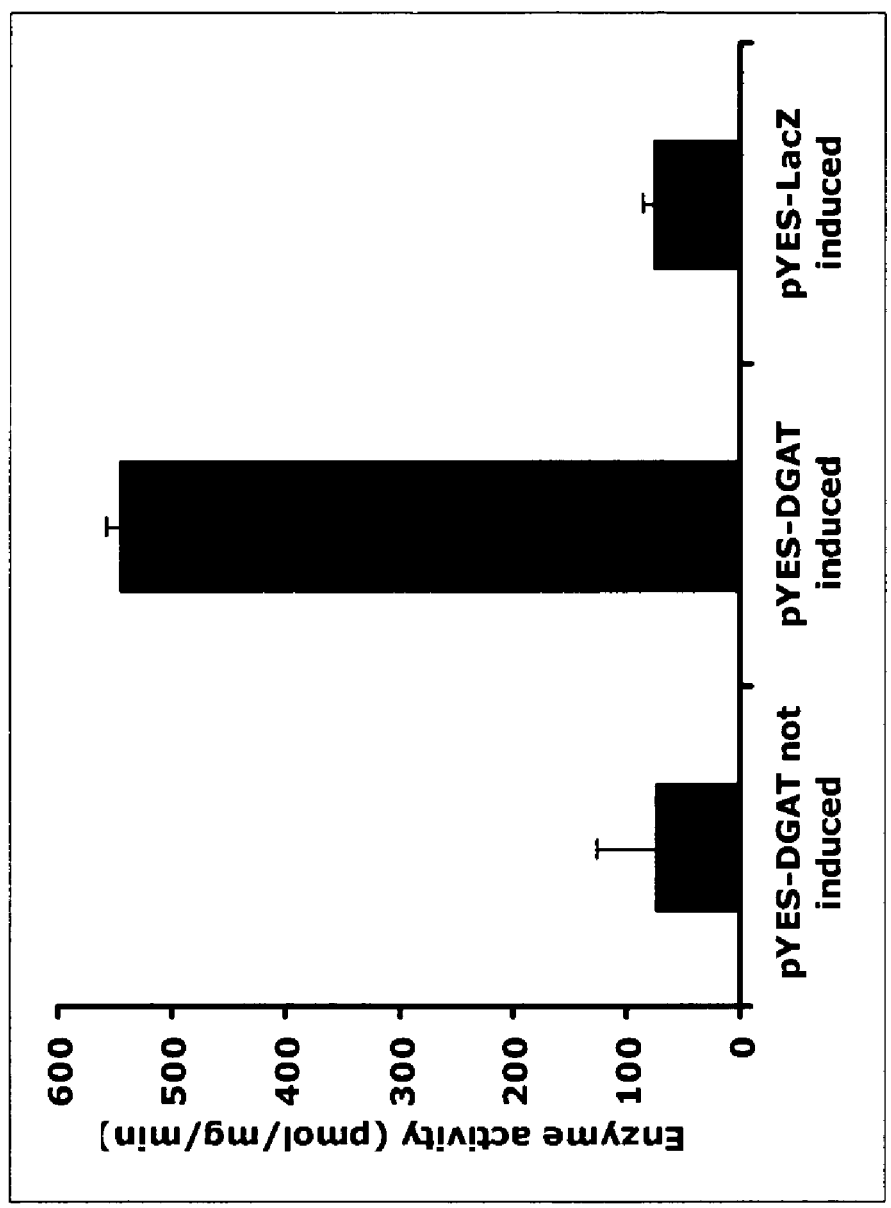

FIG. 3 shows DGAT activities measured based on the $^{14}C$-label incorporated into the TAG products. Values are means of three replicate experiments with standard deviation (SD).

Figure 4:
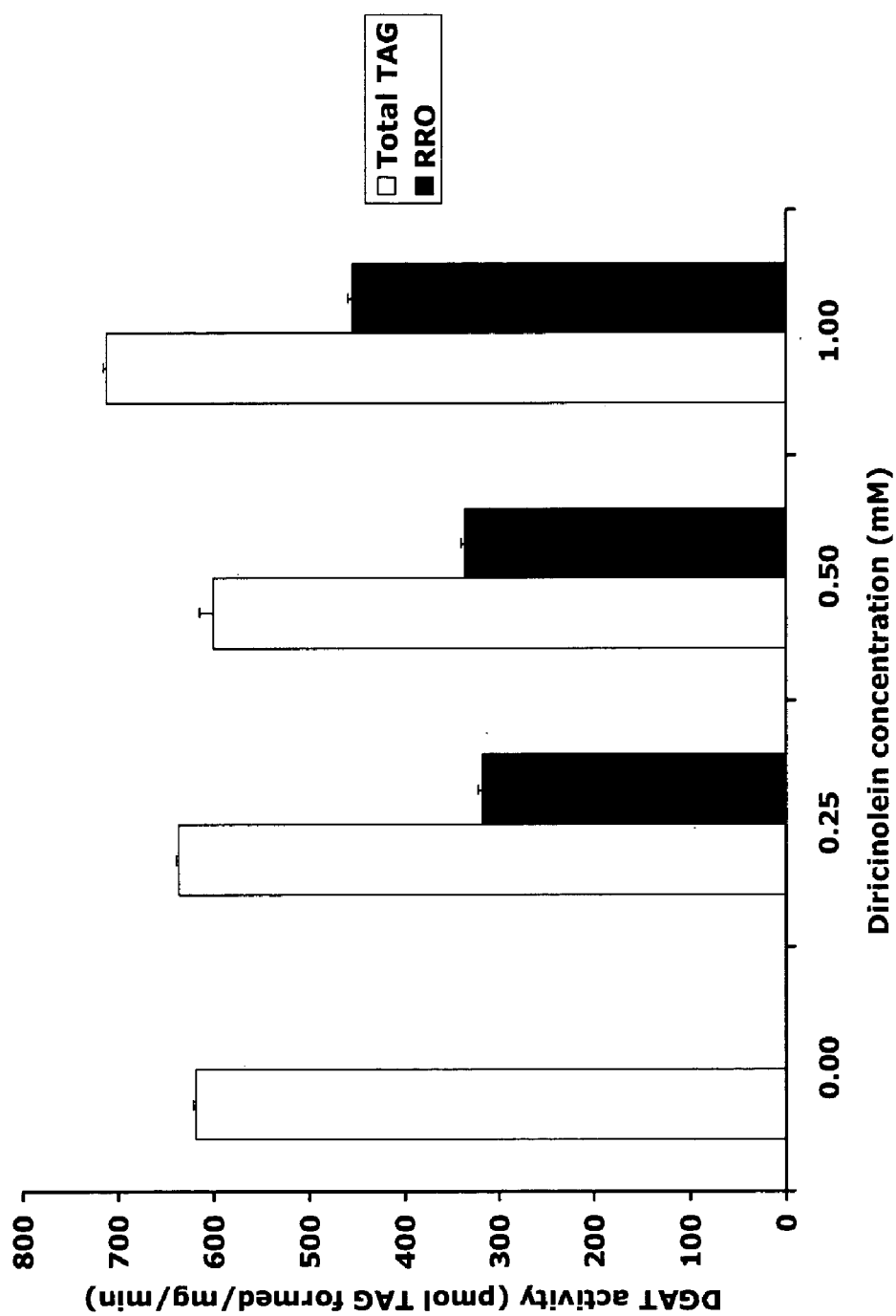

FIG. 4 shows specificity of RcDGAT for molecular species of diacylglycerol. Batches of microsomes (100 µg of total microsomal protein) extracted from yeast cells expressing RcDGAT were used in the assay. The microsomes were supplied with diricinolein and incubated with $^{14}C$-oleoyl-CoA in 100 µl of 0.1 M Tris-HCl, pH7.0 containing 20% glycerol for 15 min at 30° C. The assay was then terminated by addition of CHCl3/CH3OH (1:2, v/v). DGAT activities were determined based on the $^{14}C$-label incorporated into the TAG products. Values are means of three replicate experiments with SD. The abbreviation RRO indicates diricinoleoyloleoylglycerol.

Figure 5:
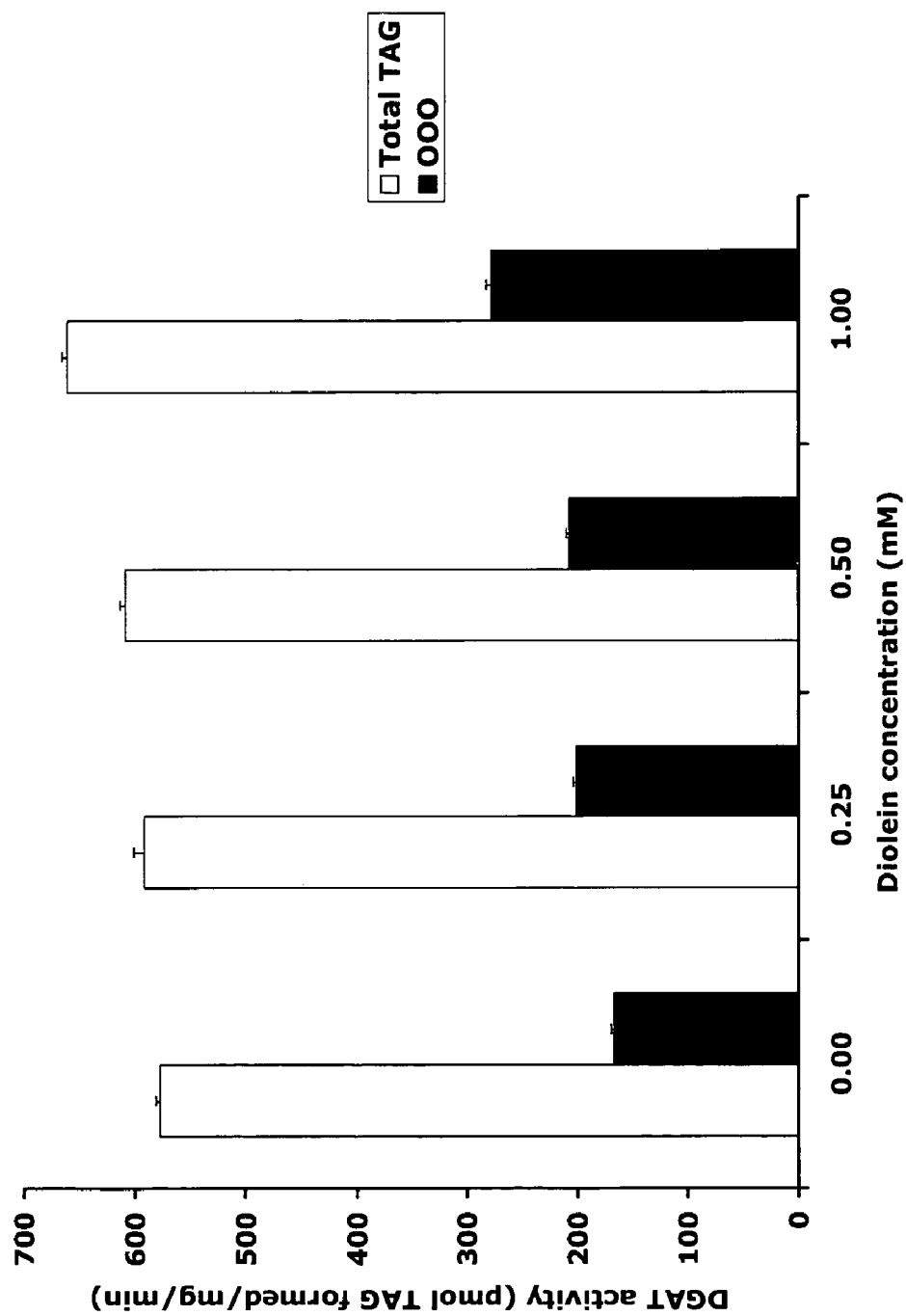

FIG. 5 shows an assay similar to FIG. 4, except the substrate was diolein. The abbreviation OOO indicates triolein.

Figure 6:
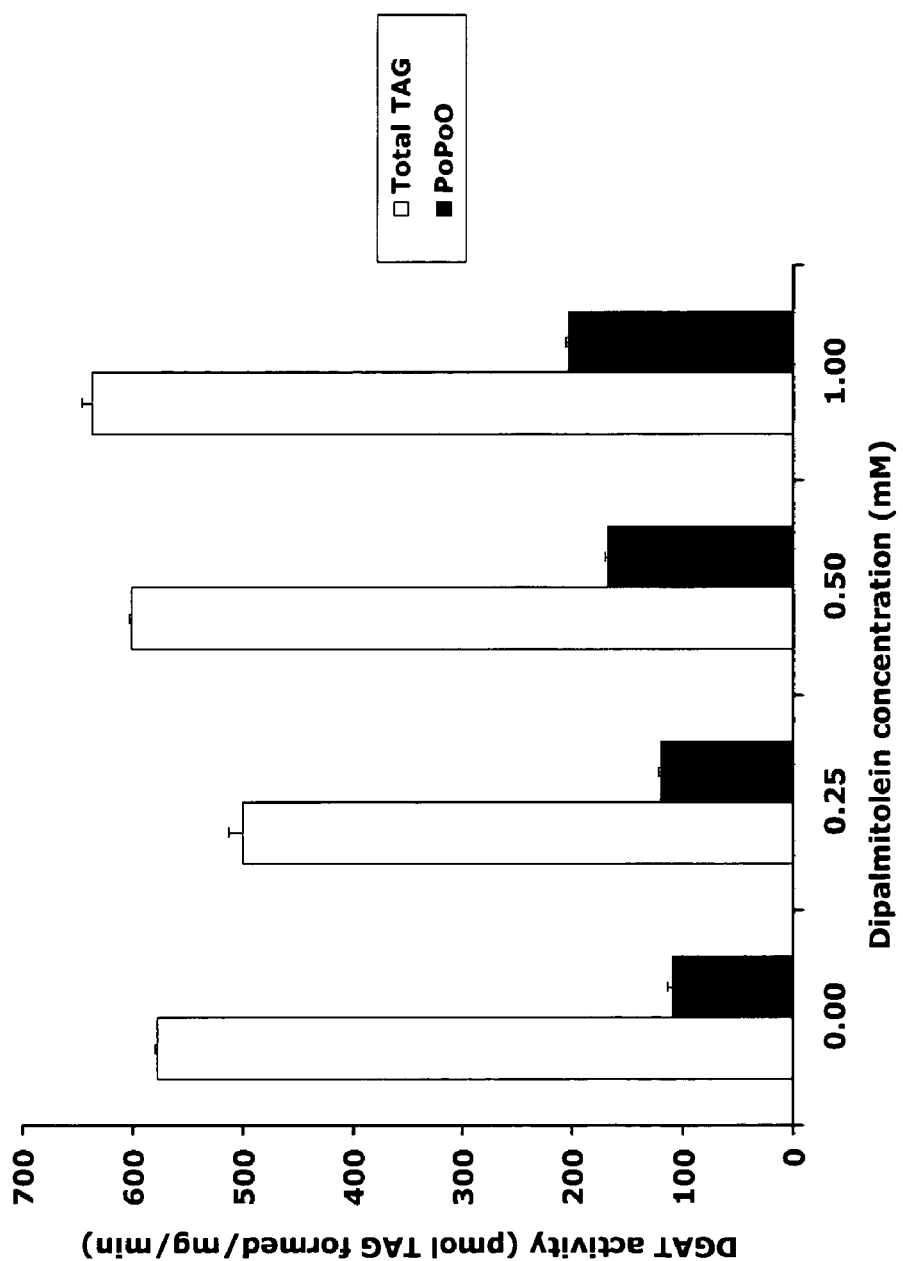

FIG. 6 shows an assay similar to FIG. 4, except the substrate was dipalmitolein. The abbreviation PoPoO indicates dipalmitoyloleoylglycerol.

Figure 7:
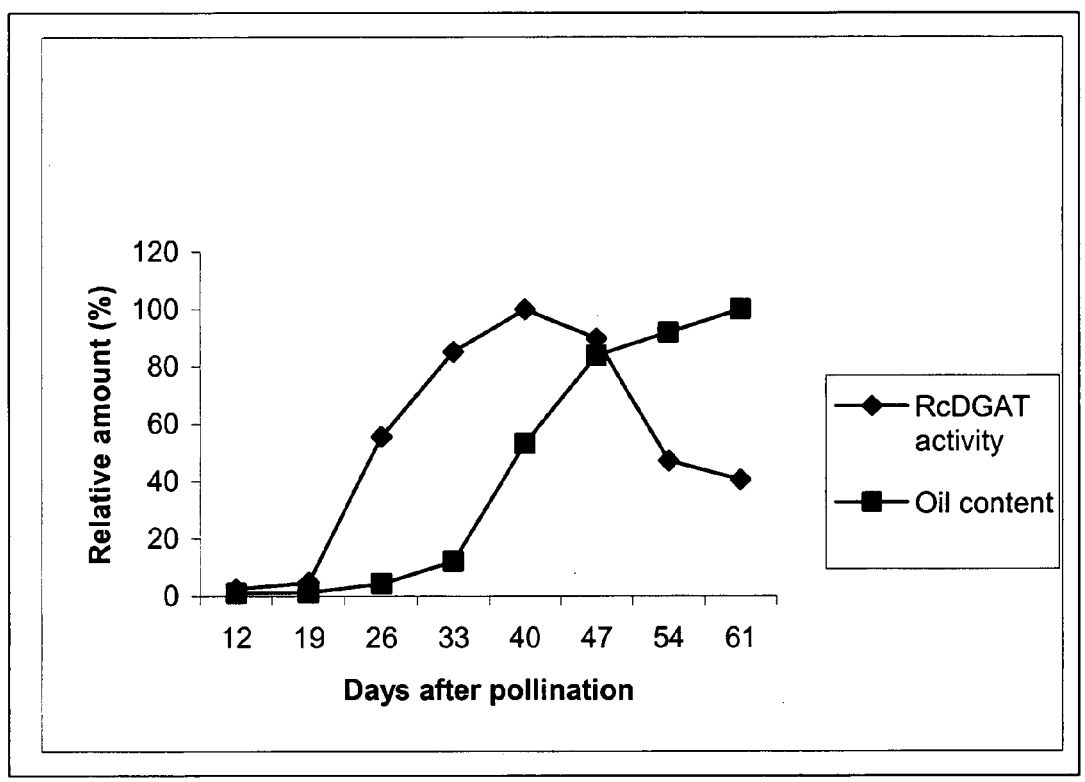

FIG. 7 shows correlation between RcDGAT activity and oil content.

BRIEF DESCRIPTION OF THE SEQUENCES

SEQ ID NO: 1 is the cDNA for RcDGAT.
SEQ ID NO: 2 is the amino acid sequence for the enzyme RcDGAT.
SEQ ID NO: 3 is a 5' end primer used to amplify the FAH gene.
SEQ ID NO: 4 is a 3' end primer used to amplify the FAH gene.
SEQ ID NO: 5 is a 5' end primer used to amplify the actin gene.
SEQ ID NO: 6 is a 3' end primer used to amplify the actin gene.
SEQ ID NO: 7 is a 3' end primer used to amplify the full-length RcDGAT cDNA.
SEQ ID NO: 8 is a degenerate primer based on the highly conserved amino sequence region, APTLCY of DGATs, and used to clone the RcDGAT gene.
SEQ ID NO: 9 is a degenerate primer based on the highly conserved amino sequence region, WNMPVHKW of DGATs, and used to clone the RcDGAT gene.
SEQ ID NO: 10 is a 5' end primer used to amplify the RcDGAT gene and clone this gene into the yeast vector pYES2.1/V5-His-TOPO for expression of RcDGAT gene in yeast cells.
SEQ ID NO: 11 is a 3' end primer used to amplify the RcDGAT gene and clone this gene into the yeast vector pYES2.1/V5-His-TOPO for expression of RcDGAT gene in yeast cells.

DEFINITIONS

DAG is diacylglycerol
DGAT is diacylglycerol acyltransferase.
FAH is fatty acyl hydroxylase.
RcDGAT is diacylglycerol acyltransferase from *Ricinus communis*.
TAG is triacylglycerol.
DAP is days after pollination.
"Transformation" refers to the permanent, heritable alteration in a cell resulting from the uptake and incorporation of foreign DNA into the host-cell genome; also, the transfer of an exogenous gene from one organism into the genome of another organism.

"Transgenic" refers to a cloned gene that is introduced and stably incorporated into the genome of a plant or animal and is passed on to successive generations. A "transgenic organism" is an organism whose genome has been transformed by the introduction and stable incorporation of exogenous DNA.

"Exogenous DNA" is defined as DNA or polynucleotides deriving from a source other than the genome to which said polynucleotides have been introduced and incorporated therein.

"Oilseed plants" are defined as plants producing commercially-important vegetable oil such as canola, rapeseed, castor bean, and soybean.

"Micro-organisms" include but are not limited to bacteria, fungi, protozoans, viruses, and microscopic algae.

An "appropriate vector" is an agent, generally a plasmid or virus, used to transmit genetic material to a cell or organism. A cloning vector may include a small DNA molecule, usually derived from a bacteriophage or plasmid, which is used to carry a fragment of DNA to be cloned into the recipient cell, and which enables the DNA fragment to be replicated.

"Sequence identity" generally means the percent overlap or degree of commonality between molecules being compared. It is generally used when comparing the type and particular order of polynucleotide base pairs and/or amino acids.

DETAILED DESCRIPTION OF THE INVENTION

Castor oil is extremely viscous and is an excellent source for biodegradable lubricants and greases. Unfortunately, extracting castor oil from the castor plant (*Ricinus commu-* nis) is problematic because the plant also contains the toxin ricin as well as various allergens which can be quite harmful.

The favorable properties of castor oil are due to the presence of ricinoleate, which is the salt form of ricinoleic acid, a hydroxy fatty acid that comprises approximately 90% of the fatty acid composition in castor oil. Like most mono-unsaturated fatty acids, the double bond in the hydrocarbon chain of ricinoleic acid occurs between the 9th and 10th carbon atom on the chain. What imparts the unique physical and chemical properties to ricinoleic acid is a hydroxyl group (—OH) on the 12th carbon of the molecule. This results in enhanced viscosity of ricinoleate-containing oils.

Little is known about the mechanisms responsible for the high amounts of ricinoleate in castor oil. It has been proposed that the diacylglycerol (DGAT) of any particular plant may have structural features that enable them to efficiently acylate with the fatty acids that predominate in the plant. There have been a number of studies regarding selectivities for substrates by castor DGAT. For example, acylation activity in microsomes from *Ricinus communis* endosperm clearly demonstrated a preference for inserting ricinoleate into TAG, while the same substrate was not efficiently used by other plant species. The inventors' previous research also demonstrated that castor endosperm microsomes have a strong preference for incorporating ricinoleate into TAG in comparison to oleate and other fatty acids. However, all these conclusions were drawn from the microsomal enzyme assays. Because there are a number of pronounced metabolic activities present in the castor microsomes, it is difficult to evaluate the particular role of RcDGAT in castor oil biosynthesis using this system. Therefore isolation of the gene becomes necessary.

Genes encoding DGAT have been cloned and characterized from several plant species, but the gene coding for RcDGAT in castor bean has never been previously identified and cloned. The inventors have identified and cloned the RcDGAT gene from developing castor seeds. It is identified as SEQ ID NO: 1 and is found in appendix A. Furthermore, the RcDGAT gene has been isolated, incorporated into a vector, and deposited with the ARS (NRRL) Culture Collection. Accession No. NRRL B30749 deposited on Jun. 2, 2004.

Analysis of the RcDGAT gene sequence reveals that this cDNA encodes a protein of 521 amino acids with a molecular mass of 59.9 kDa. See SEQ ID NO: 2.

The cDNA sequence for RcDGAT is similar to, but distinguishable from, cDNA sequences which code for other Acyl CoA:diacylglycerol acyltransferase (DGAT), the significance of which is set forth below.

DGAT is a transmembrane enzyme which catalyzes the final step in the Kennedy pathway for triacylglycerol (TAG) biosynthesis and has been proposed to be the rate-limiting enzyme in plant storage lipid accumulation. DGAT is implicated in various other cellular processes as well. For example, an *Arabidopsis* mutant deficient in DGAT activity results in reduced TAG content, delayed seed development, and altered seed fatty acid composition, while overexpression of DGAT in *Arabidopsis* seeds results in enhanced oil deposition and seed weight.

RcDGAT contains a unique site not found in other DGATs; that is, the binding-protein-dependent transport systems inner membrane component, residing in residues 219–247. See FIG. 1. The significance of the presence of this signature in vivo is unknown. In bacteria, such sites often interact with a binding protein allowing transmembrane transport. We speculate that this site in RcDGAT would interact with the acyl-CoA substrates bound to acyl-CoA binding proteins and determine the capability of RcDGAT to selectively interact with ricinoleoyl substrates.

Figure 2B:
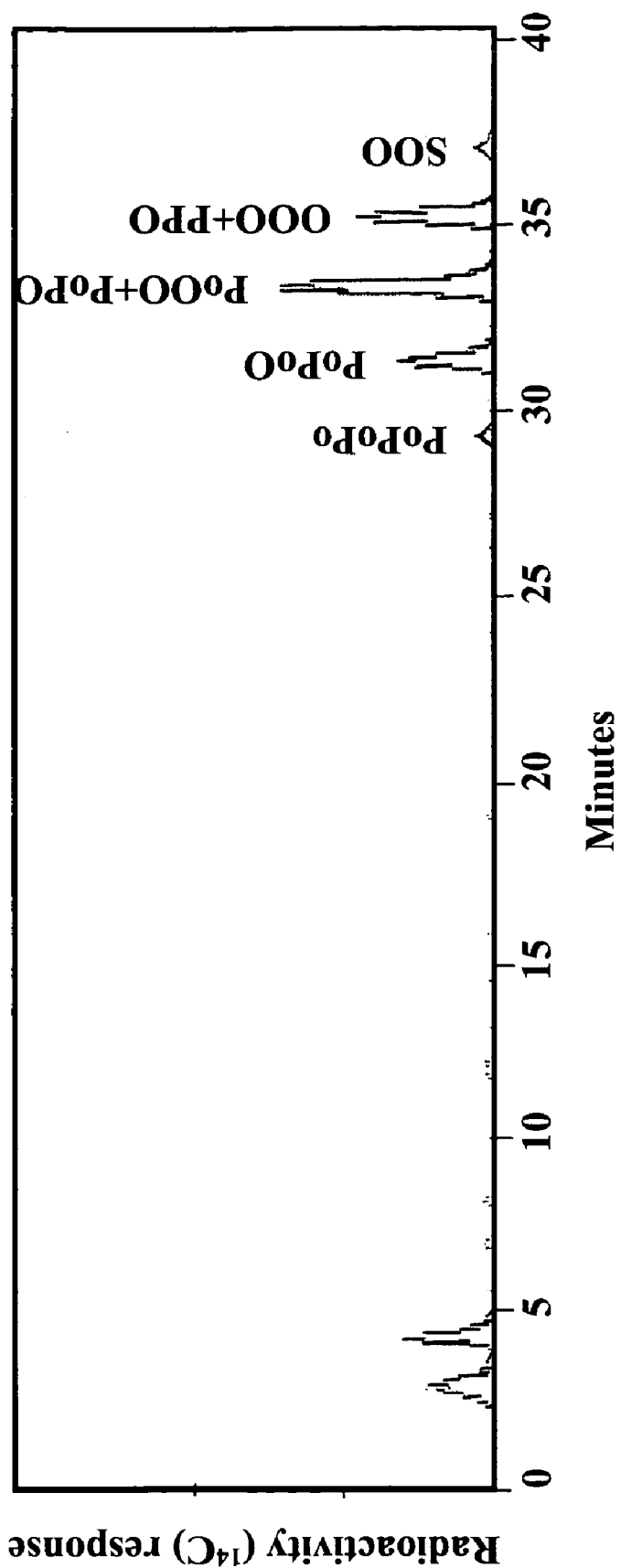

While RcDGAT activity has been previously identified in an environment with a mixture of multiple enzymes (castor microsome), it has never been isolated from castor and studied in a heterologous system. The inventors selected a yeast cell system to study the gene function of RcDGAT because this system has the benefit of low fat content and low biosynthetic capacity. The most abundant fatty acids in the yeast cells are oleate, palmitoleate, palmitate and stearate FIGS. 2A and B. It is very easy to see the function of the target gene in the oil biosynthesis. The DGAT activity and commensurate oil biosynthesis in wild type yeast cells is very low (FIG. 2A). However, cells expressing RcDGAT exhibited much higher DGAT activity and oil production, suggesting the importance of RcDGAT in oil biosynthesis. FIG. 2B.

The inventors have discovered that the RcDGAT has pronounced selectivities for substrates containing ricinoleate (FIGS. 4, 5, and 6), leading to the incorporation of various ricinoleoyl moieties into triacylglycerols. Most plants will oxidize ricinoleate when it is produced because of the hydroxyl function. The presence of RcDGAT will provide the enzymatic mechanism essential to incorporating ricinoleate into the oil. In fact, the inventors have shown that RcDGAT is directly involved in regulation of castor oil metabolism and biosynthesis. The inventors observed that the appearance of RcDGAT activity was coincident with the onset of lipid accumulation and the maximal activity occurred during the rapid phase of lipid biosynthesis. See FIG. 7. When the lipid content of the seeds reached a plateau, the activity decreased immediately.

The inventors have also shown that the RcDGAT cloned from castor seeds encodes an active enzyme. As discussed below, when expressed in yeast *S. cerevisiae*, the RcDGAT cDNA produced a protein with a size as predicted from the nucleic acid sequence.

Therefore, expression of RcDGAT in transgenic crops with an active hydroxylase gene can result in the production of oil with high ricinoleate. As reflected in the examples below, the RcDGAT gene can be stably incorporated into a variety of recombinant hosts such as micro-organisms and plants.

EXAMPLES, REPRESENTATIVE ASSAYS, AND EXPERIMENTAL PROCEDURES

Many of the following procedures and protocols are standard and well known to those of ordinary skill in the art. Moreover, to avoid duplication and redundancy, the following patents and the teachings therein are incorporated by reference into this application and intended to provide guidance and background information to one of ordinary skill in the art: U.S. Pat. No. 6,620,986 to McKeon, U.S. Pat. No. 6,521,435 to Okubara, and U.S. Pat. No. 6,737,260 to Thomashow.

RNA Extraction and RT-PCR

RNA samples were extracted from castor seeds at different development stages using the method of Gu et al. RT-PCR was carried out using the Gibco BRL SuperScript First-Strand Synthesis System for RT-PCR (Grand Island, N.Y.). Briefly, 5 μg of total RNA was used to synthesize the first-strand cDNA using oligo(dT) primers, then 10% of the first-strand cDNA was used to amplify the target cDNAs, RcDGAT, FAH and actin using gene-specific primers. The primers for RcDGAT gene were HE-15F and HE-6R. The primers for the FAH gene are those designated as SEQ ID NO: 3 and SEQ ID NO: 4, found in the appendix. The primers for the actin gene are designated as SEQ ID NO: 5 and SEQ ID NO: 6, also found in the appendix. PCR was performed for 30 cycles with an annealing temperature of 65° C. One tenth of the PCR product was analyzed on 1% agarose gel.

To monitor the gene expression pattern of RcDGAT, RT-PCR reactions were performed. It is well known that actin is a plant housekeeping gene and its expression level correlates well with total RNA during different development stages. The results from actin RT-PCR suggested that the efficiencies of RT-PCR among samples are uniform in this system. The results revealed that the accumulation patterns of RcDGAT and FAH mRNA were very different although both of them encode enzymes for castor oil biosynthesis. The amount of RcDGAT mRNA is maximal at an early stage of seed development (19 DAP), and declined thereafter, while the FAH mRNA was maximal at a later stage (33 DAP) of seed development and continued until 47 DAP.

There is evidence indicating that genes involved in storage product synthesis are concomitantly expressed, and it has been reported that the in vitro activities of diacylglycerol acyltransferases peak during the active period of TAG accumulation (around 30 DAP). Thus the mRNA for RcDGAT may encode a stable protein and, accordingly, its level would not correlate with RcDGAT protein level and enzyme activity, or the enzyme activity may be post-transcriptionally controlled. As a matter of fact, there are multiple potential phosphorylation sites based on functional motifs and critical amino acid residues in the deduced amino acid sequence of RcDGAT. This suggests that the enzyme activity could be regulated by some specific protein kinases. Additionally, a second DGAT may exist and play a role in oil formation at later stages of seed. Alternatively, RcDGAT may be involved in some other processes in the early stages of seed development. In mammalian systems for example, DGAT can remove diacylglycerol, a signaling molecule in the phospholipase C-inositol phospholipid cascade by converting it to TAG. It is possible then, that DGAT in plants serves additional roles beyond oil biosynthesis and the expression pattern of RcDGAT could reflect one such role. RcDGAT mRNA was also detected in vegetative tissues such as roots, stems, cotyledons and true leaves. The importance of RcDGAT in these tissues is unknown.

Southern Blot Analysis.

In order to determine the copy number of RcDGAT gene in castor plants, Southern blot analysis of genomic DNA was conducted under high stringency hybridization conditions. Castor genomic DNA was isolated from leaves using the CTAB procedure. Southern blot analysis was carried out according to DIG application manual for hybridization of DNA probes to a Southern blot (Roche, Indianapolis, Ind.). DNA samples (3 μg) were separated on a 1% TAE agarose gel, then transferred to a positively charged nylon membrane (Roche, Indianapolis, Ind.). The filter was hybridized to a DIG-labeled DNA probe amplified from RcDGAT cDNA by PCR using primers HE-15F (SEQ ID NO: 5) and HE-6R (SEQ ID NO: 7).

The results from the restriction enzyme digestion patterns of HindIII, SmaI, XhoI, and PvuII suggest that RcDGAT is a single copy gene in castor. A single band was detected with restriction enzymes HindIII, SmaI and XhoI and two bands were detected with PvuII due to the presence of an internal cutting site. However, two bands were detected with PstI although there is no cutting site in the cDNA sequence. This may be due to the presence of a PstI site in intron regions. Six randomly selected RcDGAT cDNAs were sequenced and found to be identical, providing further evidence that RcDGAT is a single copy gene in castor genome.

Cloning of a cDNA Encoding DGAT from *R. communis*

The cloning of RcDGAT made it possible to elucidate the individual role of this particular enzyme in castor oil biosynthesis.

A 378 base pair (bp) fragment of RcDGAT cDNA was amplified from RNA samples extracted from castor seeds by RT-PCR using two degenerate primers, designated SEQ ID NO: 8 and SEQ ID NO: 9. These two primers were designed based on the highly conserved amino acid sequence regions, APTLCY and WNMPVHKW of DGATs. The sequence information obtained from the 378 bp cDNA fragment was then used to generate gene-specific primers for 3' and 5'-RACE (rapid amplification of cDNA ends). Using the known sequence information obtained from 3'- and 5'-RACE, primers were designed for end-to-end amplification of the complete gene from the RACE-ready cDNA template following the manufacturer's instruction (Invitrogen, Carlsbad, Calif.). The full-length cDNA was completely sequenced in both directions using a Perkin Elmer Big Dye sequencing kit (Perkin Elmer, UK). See SEQ ID NO: 1.

Sequence alignment and similarity among species were determined using Clustal W program available online at http://pbil.ibcp.fr/NPSA/npsa_prosite.html. The protein motifs were identified using ScanProsite at http://www.expasy.ch/tools/scnpsit1.html.

Relationship of RcDGAT to Other DGAT

Using degenerate primers, a DNA fragment of 378 bp was amplified from castor seeds by RT-PCR and sequenced. Based on the sequence information, gene-specific primers for 3'- and 5'-RACE were designed, yielding a full-length cDNA. Sequence analysis indicates that the castor DGAT cDNA (RcDGAT) is 2067 bp long with 266 bp 5'- and 235 bp 3'-end untranslated regions (GenBank accession number AY366496). See SEQ ID NO: 1. This cDNA is predicted to encode a protein of 521 amino acids with a molecular mass of 59.9 kDa. See SEQ ID NO: 2.

Conserved regions of DGAT from five different plant species (RcDGAT and four others—*A. thaliana* [AtDGAT], *B. napus* [BnDGAT], *N. tobacum* [NtDGAT], and *T. majus* [TmDGAT]) were identified by sequence alignment of deduced amino acid sequences. When all five DGATs were aligned, their amino acid identity reaches 50.18% with the most conserved regions in the C terminus (63.27% identity within 422 amino acids), while the first 119 N-terminal amino acid residues only share 5.88% identity (FIG. 1). The major functional point in common for these DGATs is their ability to interact with fatty acyl CoA and diacylglycerol.

The nucleic acid sequence of RcDGAT shares approximately 69–71% identity with other cloned plant DGATs. FIG. 1. Percentage of identity between two DGAT gene sequences when aligned using Lipman and Pearson's Align program (http://molbiol.soton.ac.uk/compute/align.html) were as follows:

|  | AtDGAT | BnDGAT | NtDGAT | TmDGAT |
| --- | --- | --- | --- | --- |
| RcDGAT | 69.2% | 68.3% | 69.6% | 70.5% |

The castor sequence, with different phosphorylation and glycosylation sites, and a unique binding protein site, correlates with its unique capability of producing high levels of ricinoleoyl TAGs.

Identification of Putative Functional Motifs in RcDGAT.

Searches of the protein databases indicated that the predicted RcDGAT protein has an isoelectric point of 8.39 (predicted by Protparam at http://www.expasy.ch) and thus is positively charged at neutral pH. The deduced amino acid sequence of RcDGAT contained three potential N-linked glycosylation sites (N—X—S/T) which were also present in the TmDGAT and NtDGAT, but not in the AtDGAT and BnDGAT. Since the RcDGAT protein expressed in yeast cells matched the predicted molecular size, and treatment with glycosidase had no effect on electrophoretic migration, it appeared that RcDGAT was not glycosylated. In addition, RcDGAT contains a unique site, that is, the binding-protein-dependent transport systems inner membrane component signature, residing in residues 219–247. In bacteria, such sites often interact with a binding protein allowing transmembrane transport. This site in RcDGAT could interact with the acyl-CoA substrates bound to acyl-CoA binding proteins, and may therefore be involved in the specificity of RcDGAT. The only notable structures that RcDGAT shares in common with other plant DGATs cloned to date are the multiple transmembrane domains in the C terminal conserved regions, consistent with an integral membrane enzyme.

Specificity of RcDGAT for Molecular Species of Diacylglycerol

The inventors examined the effectiveness of RcDGAT in using different molecular species of DAG for TAG. The substrates 1,2-diolein, 1,2-dipalmitolein and 1,2-diricinolein were incubated with yeast microsomes and $^{14}$C-oleoyl-CoA. See FIGS. 5 and 6. RcDGAT activities were then determined. The addition of different molecular species of DAG up to 1 mM to the microsomal mixture had little effect on the amount of total TAG formed in the assay. However, the RcDGAT clearly demonstrated a preference for diricinoleins. See FIG. 4. With the addition of 0.25 mM DAG the amount of RRO from diricinolein increased 318 pmole/mg/min, while the amount of OOO from diolein and PoPoO from dipalmitolein only increased 34 and 10 pmol/mg/min compared to that without exogenous DAG. See FIGS. 5 and 6. Although complicated by the presence of endogenous diolein and dipalmitolein in the yeast cells, the absolute incorporation of oleate into RRO was still much higher than OOO and PoPoO (456 vs. 278 and 204 pmol/mg/min, with 1 mM of DAG). DGAT activity was also measured using microsomes from yeast cells carrying RcDGAT gene but grown under a repression condition. The absolute incorporation of $^{14}$C-oleate into RRO was less than 20 pmol/mg/min in the presence of 1 mM diricinolein. This result suggested that the RRO present in RcDGAT containing microsomes was mostly generated by RcDGAT, instead of yeast endogenous DGAT. Previous studies of isolated castor microsomes suggest that the final acylation step in castor oil biosynthesis displays a strong preference for diricinolein vs. other DAG. There has been considerable debate, however, about which enzyme carries out this step. The enzyme phospholipid diacylglycerolacyl transferase (PDAT) has been widely believed to be responsible. (Banas et. al. 2000).

There are several reports in the literature describing castor DGAT substrate specificity using castor microsomes. It is difficult, however, to conclude that the substrate specificity is solely due to a single enzyme in the castor microsomes, since there are a number of activities present that can contribute to the end product. Hence, the substrate specificity of this enzyme was investigated in a yeast cell system which has the benefit of low fat content and biosynthetic capacity. By applying diricinolein and other DAG substrates in the assay, it was discovered that the RcDGAT exhibited much higher activity with diricinolein than with diolein and dipalmitolein. The information presented here has significant importance for better understanding the regulation of triricinolein biosynthesis in castor plants and provide a valuable means for engineering crops containing high levels of hydroxylated fatty acids.

Western Blot Analysis

Microsomal samples (30 μg of total protein) from RcDGAT- or LacZ-transformed yeast were separated by SDS-PAGE and electrotransfered onto PVDF membranes. The membranes were incubated with the anti-V5 antibodies (Invitrogen, Carlsbad, Calif.) at 1:5000 dilution and horseradish peroxidase-conjugated goat-anti-mouse secondary antibodies (Roche, Indianapolis, Ind.) at 1:1000 dilution. Horseradish peroxidase activity was visualized by chemiluminescence using the ECL kit (Amersham, Arlington Heights, Ill.).

Western blot analysis revealed that the cloned RcDGAT cDNA was expressed at a high level in yeast cells and the gene product appeared mainly as full-length proteins.

Cells transformed with the plasmid carrying RcDGAT cDNA expressed a ~65-kDa protein (V5 epitope and the polyhistidine tag from the vector add approximately 5-kDa to the size of the protein) when induced with 2% galactose but this protein was not detected in the same cells grown under 2% glucose.

Functional Expression of RcDGAT in Yeast.

The RcDGAT coding region was subcloned into a pYES2.1/V5-His-TOPO vector and transformed into S. cerevisiae strain INSc1 according to the manufacturer's instruction (Invitogen, Carlsbad, Calif.). The primers used are identified as SEQ ID NO: 10 and SEQ ID NO: 11.

In order to ensure that the insertion contained a yeast consensus sequence for initiation of translation, (G/A) NNATGG, the second amino acid codon was changed from acg (threonine) to ggg (glycine). The translation stop site (5'-TGA-3') was removed to fuse RcDGAT in frame with the V5 epitope and polyhistidine tag for detection and purification of the protein. A single colony containing pYES2.1/V5-His/RcDGAT or pYES2.1/V5-His/lacZ construct was inoculated into medium containing 2% glucose and grown overnight at 30° C. with shaking. 2% galactose was added to the medium to induce expression of the recombinant proteins from the GAL1 promoter. Cells were harvested at 14 hours after induction and the cell pellets were stored at −80° C. until ready to use.

Microsomes were isolated from cells after 14 hours induction with 2% galactose and DGAT activity was determined by measuring the incorporation of $^{14}$C-oleoyl-CoA into TAG. As negative controls, DGAT activities in cells with pYES2.1/V5-His/RcDGAT grown under the repression (2% glucose) condition and with pYES2.1/V5-His/lacZ grown under the induction (2% galactose) condition were measured. FIGS. 2A and 2B show the separation of the molecular species of $^{14}$C-TAG extracted from yeast microsomal incubation on C18 HPLC. The five $^{14}$C peaks labeled were identified by matching the retention times of the TAG identified previously and fatty acid compositions of the yeast microsomes examined by GC analyses of fatty acid methyl esters. The major molecular species of TAG predicted in the yeast cells are PoPoPo, PoPoO, PoOO, PoPO, OOO, PPO, and SOO (Po—palmitoleate, P— palmitate, O— oleate, S—stearate). Cells expressing RcDGAT exhibited more than 7-fold higher DGAT activity in comparison to controls. See FIG. 3. Wild type yeast cells, for example, had low DGAT activity in the system tested. Others have observed (Bouvier-Nave et al.) that expression of the *Arabidopsis* DGAT in yeast resulted in the formation of a floating layer on top of the 100,000 g supernatant during the preparation of microsomes which displayed extremely high DGAT activity. We also observed a thin floating layer on top of the 100,000 g supernatant during the RcDGAT-transformed yeast microsomal isolation which exhibited some DGAT activity, but the activity was much lower than the microsomal fraction.

Assay for DGAT Activity.

Microsomes were isolated from harvested yeast cells as described by Urban et al. and resuspended in 0.1 M Tris-HCl, pH7.0 containing 20% glycerol (5 mg protein/ml) and kept frozen at −80° C. Protein concentration was determined using Bicinchoninic Acid (BCA) protein assay kit (Pierce, Rockford, Ill. 61105). DGAT assays were performed as in Cases et al. 14C-Oleoyl-CoA was synthesized according to McKeon et al. (1997). The reaction mixture (100 μl) consisted of 0.1 M Tris-HCl, pH7.0 containing 20% glycerol, microsomes (100 μg of protein) and 14C-oleoyl-CoA (20 μM, 200,000 c.p.m.) and was incubated for 15 min at 30° C. In assays for substrate specificity of RcDGAT, different molecular species of DAG dissolved in 5 μl of methanol were added to the above reaction mixture (concentration from 0 to 1.0 mM). The reactions were stopped and lipids were extracted using standard techniques involving chloroform/methanol. Different molecular species of TAG products were separated from free fatty acids using C18 HPLC (25×0.46 cm, 5 μm, Ultrasphere C18, Beckman Instruments Inc., Fullerton, Calif.). DGAT activity (pmole TAG formed/ mg protein/min) was determined based on the 14C-label incorporated into the TAG products from 14C-oleoyl-CoA.

Inserting RcDGAT and the FAH Gene into Micro-Organisms

As previously described, the inventors successfully introduced RcDGAT into yeast.

Other micro-organisms have also been transformed with RcDGAT such as oleaginous and other fungi capable of producing traicylglycerols as storage lipid. These include *Saccharomyces* sp., *Mortierella alpine*, and *Mucor circinelloides*.

To express FAH and RcDGAT genes in microbes, these genes' coding regions were subcloned into appropriate vectors, then electronically transformed into the target organisms. For example, to generate transgenic yeast, the RcDGAT gene was cloned into the pYES2.1/V5-His-TOPO vector (Invitrogen, Carlsbad, Calif.) and then transformed into *S. cerevisiae* strain INVSc1 according to the manufacturer's instruction (Invitogen, Carlsbad, Calif.). The primers used were those described in SEQ ID NO: 10 and 11. The above-mentioned control sequences were operably linked to the nucleic acids comprising the FAH and RcDGAT genes.

In order to ensure that the insertion contains a yeast consensus sequence for initiation of translation, (G/A) NNATGG, the second amino acid codon was changed from acg (threonine) to ggg (glycine). The translation stop site (5'-TGA-3') was removed to fuse RcDGAT in frame with the V5 epitope and polyhistidine tag for detection and purification of the protein.

Using RcDGAT and FAH with Oilseed Crops

In order to engineer higher content of hydroxy and other industrial use fatty acids in commodity vegetable oils, the RcDGAT gene was inserted into oilseed crops such as soybean (*Glycine max*), rapeseed, canola, *Arabidopsis* and other plants of the Brassicaceae flax (*Linum* sp.), and castor (*Ricinus communis*).

In addition to preparing microbial vectors as described above, the technique used to insert the FAH gene and RcDGAT gene also involved cloning the genes into the binary vector pCambia0380 under transcriptional control of AtDGAT promoter. The AtDGAT promoter was amplified by PCR from *Arabidopsis thaliana* genomic DNA using primers designed from the available sequence (Lu et al. 2003).

Transgenic plants were then generated by the standard *Agrobacterium*-mediated transformation method described in Clough and Bent (1998), the teachings and citations of which are incorporated herein by reference.

Various Diacylglycerol Substrates Have Been Transformed with RcDGAT

Various diacylglycerol substrates in plants and microbes have been used to produce TAG using RcDGAT. These include diacylglycerol substrates containing (a) polar functional groups (-hydroxy FA, dihydroxy FA, and polyhydroxy FA in any carbon-chain position, from chain lengths of 4 to 26 carbons); (b) epoxy groups in any position (-epoxy, diepoxy, and polyepoxy); (c) conjugated fatty acids with 2 to 6 double bonds in conjugation (-acetylenic FA, diacetylenic FA and polyacetylenic FA; (d) fatty acids with triple bond in any position; (e) any combination of these and any other polar FA for which the RcDGAT is capable of directing the incorporation of such FA into oil; and (f) any other industrially used fatty acid for which RcDGAT is capable of directing its incorporation into oil.

What is claimed is:

1. An isolated nucleic acid molecule encoding a polypeptide having diacylglycerol acyltransferase (DGAT) activity selected from the group consisting of:

a. a nucleotide sequence as given in SEQ ID NO:1;

b. a nucleotide sequence as given in SEQ ID NO:1 from nucleotide 267 to nucleotide 1825;

c. a nucleotide sequence having at least 95% sequence identity with SEQ ID NO:1 from nucleotide 267 to nucleotide 1825;

d. a nucleotide sequence encoding a polypeptide having an amino acid sequence of SEQ ID NO:2; and e. a nucleotide sequence encoding a polypeptide having an amino acid sequence which has at least 95% amino acid sequence identity with SEQ ID NO:2.

2. A nucleic acid construct comprising a nucleic acid molecule of claim 1 operably linked to one or more control sequences which direct the production of a polypeptide having DGAT activity in an expression host.

3. A yeast or oleaginous fungal cell transformed with the nucleotide sequence of claim 1.

4. A micro-organism transformed with the nucleotide sequence of claim 1.

5. A transgenic organism transformed by the introduction of an isolated polynucleotide, of claim 1, wherein the transgenic organism is selected from the group consisting of:

a. yeast;
b. *Mortierella alpine*; and
c. *Mucor circinelloides*.

6. A method of transforming a micro-organism by stably incorporating a nucleic acid molecule of claim 1 into said micro-organism, comprising the steps of:
   a. cloning said nucleic acid molecule into an appropriate vector; and
   b. transforming the micro-organism with said vector.

7. A method for producing a polypeptide having diacylglycerol acyltransferase (DGAT) activity, which comprises cultivating a recombinant host comprising a transformed cell having a nucleic acid molecule of claim 1 under conditions suitable for production of the polypeptide.

8. The method of claim 7, wherein the recombinant host is a micro-organism.

* * * * *